(12) United States Patent
Pfenniger et al.

(10) Patent No.: US 10,037,354 B2
(45) Date of Patent: Jul. 31, 2018

(54) SYSTEM FOR OPTIMIZING GUIDE VALUES

(71) Applicant: MEDELA HOLDING AG, Baar (CH)

(72) Inventors: Erich Pfenniger, Ebikon (CH); Beda Weber, Sins (CH); Claudius Dietzsch, Langnau am Albis (CH); Peter Vischer, Küssnacht am Rigi (CH)

(73) Assignee: MEDELA HOLDING AG, Baar (CH)

( * ) Notice: Subject to any disclaimer, the term of this patent is extended or adjusted under 35 U.S.C. 154(b) by 273 days.

(21) Appl. No.: 15/025,439

(22) PCT Filed: Sep. 26, 2014

(86) PCT No.: PCT/EP2014/070695
§ 371 (c)(1),
(2) Date: Mar. 28, 2016

(87) PCT Pub. No.: WO2015/049182
PCT Pub. Date: Apr. 9, 2015

(65) Prior Publication Data
US 2016/0224611 A1   Aug. 4, 2016

(30) Foreign Application Priority Data
Oct. 1, 2013   (EP) ..................................... 13186849

(51) Int. Cl.
*G06F 17/30* (2006.01)
*G16H 40/63* (2018.01)
(Continued)

(52) U.S. Cl.
CPC ....... *G06F 17/30371* (2013.01); *G16H 10/60* (2018.01); *G16H 40/63* (2018.01);
(Continued)

(58) Field of Classification Search
CPC ..... G06F 17/30; G06F 17/30371; G06F 17/00
(Continued)

(56) References Cited

U.S. PATENT DOCUMENTS

| 2008/0045887 | A1 | 2/2008 | Larsson et al. |
| 2008/0114870 | A1* | 5/2008 | Pu ........................ G06F 9/5077 709/224 |
| 2009/0070378 | A1 | 3/2009 | Cho et al. |

FOREIGN PATENT DOCUMENTS

| EP | 2549397 A1 | 1/2013 |
| WO | WO-01/47577 A2 | 7/2001 |

OTHER PUBLICATIONS

International Search Report for International Application No. PCT/EP2014/070695, dated Oct. 16, 2014.

* cited by examiner

*Primary Examiner* — Isaac M Woo
(74) *Attorney, Agent, or Firm* — Marshall, Gerstein & Borun LLP

(57) ABSTRACT

A system for optimizing guide values, particularly in the field of infant feeding with mother's milk and/or in the field of medical drainage, which includes at least one first data set which has at least one first data group assigned to a first target group. The system also has a second data set, with at least one second data group assigned to a second target group. First data of the first target group are stored in the at least one first data group and second data of the second target group are stored in the at least one second data group. A data processing unit is used for processing the first and second data and for output of the guide values to the second target group. The data processing unit is formed in order to receive new data generated on the basis of the output of the guide values to the second target group and on the basis of the use of these guide values in the second target group and in order to convert the first data set on the basis of these new data for the purpose of optimizing future guide values.

29 Claims, 1 Drawing Sheet

(51) Int. Cl.
*G16H 10/60* (2018.01)
*G16H 50/70* (2018.01)
*A61M 1/00* (2006.01)
*A61M 1/06* (2006.01)

(52) U.S. Cl.
CPC ........... *G16H 50/70* (2018.01); *A61M 1/0013* (2013.01); *A61M 1/0031* (2013.01); *A61M 1/06* (2013.01); *A61M 2205/50* (2013.01); *A61M 2205/52* (2013.01)

(58) Field of Classification Search
USPC .................................................. 707/600–899
See application file for complete search history.

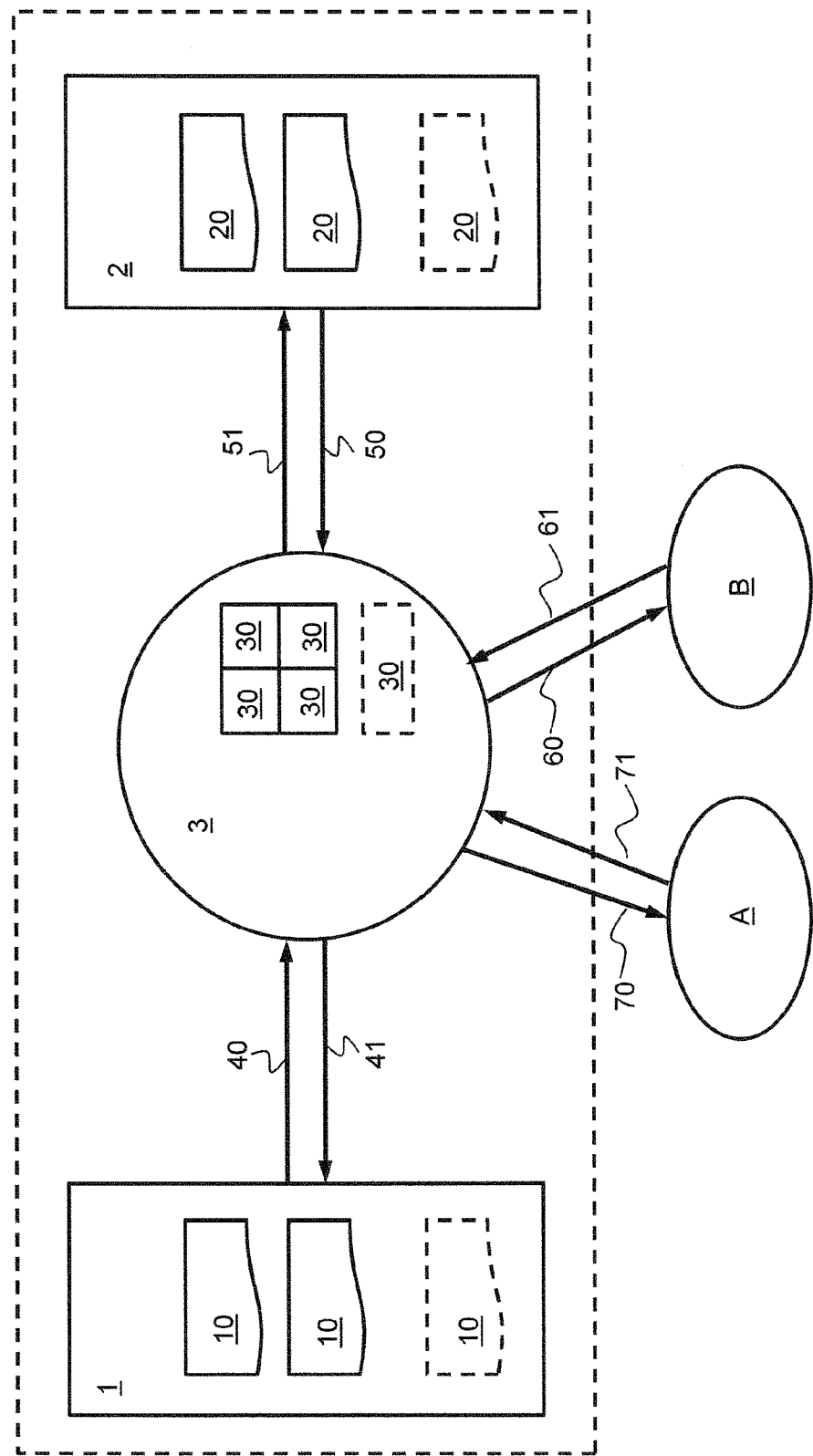

SYSTEM FOR OPTIMIZING GUIDE VALUES

CROSS-REFERENCE TO RELATED APPLICATION

The present application is the US national phase of International Patent Application No. PCT/EP2014/070695, filed Sep. 26, 2014, which application claims priority to European Application No. 13186849.9filed Oct. 1, 2013. The priority application, EP 1318649.9, is hereby incorporated by reference.

TECHNICAL FIELD

The present invention relates to a system for optimizing future guide values, particularly in the field of infant feeding with mother's milk and/or in the field of medical drainage, for example chest or wound drainage.

PRIOR ART

The optimization of breast pumps, of the process of pumping human mother's milk, as well as the giving of the pumped milk to the infant is based essentially on a mixture of empirical values and scientific research. Furthermore, the optimum depends in each case on the mother and infant, and is therefore individually different. The same also applies for medical drainage pumps, the drainage process and for treatment in other regions of the human body, or human functions.

Although devices such as breast pumps and drainage pumps are usually provided with operating instructions and recommendations for their use, their functions can usually also be adapted within certain limits to the individual requirements of the users. Furthermore, in further developments of the devices, experience from practice is acquired and is taken into account. Often, however, an overall view on the manufacturer side and the capability for individual optimization on the user side are lacking.

Platforms and forums are known from the prior art, particularly on the Internet, in which for example mothers can share their experiences. These platforms and forums, however, are usually of general nature and open to anyone. Which empirical values of other mothers she will regard as believable and recommendable, and which she will not is in this case left up to the individual mother.

SUMMARY OF THE INVENTION

It is therefore an object of the invention to provide a system which can be used for the optimization of processes, particularly in the field of infant feeding with mother's milk and/or in the field of medical drainage, for example chest or wound drainage, and which extends beyond pure information gathering of empirical values.

The system according to the invention for optimizing future guide values comprises at least one first data set which comprises at least one first data group assigned to a first target group. The system furthermore comprises at least one second data set, which comprises at least one second data group assigned to a second target group. First data of the first target group are stored in the at least one first data group and second data of the second target group are stored in the at least one second data group. The system comprises a data processing unit for processing the first and second data and for output of existing guide values to the second target group. According to the invention, the data processing unit is formed in order to receive new data generated on the basis of the output of the guide values to the second target group and on the basis of the use of these guide values in the second target group and in order to convert the first data set on the basis of these new data for the purpose of optimizing future guide values.

Existing guide values are preferably guide values which are already stored in the system. These are for example guide values entered on the producers side and which base on experiences or estimations. Alternatively or additionally, the guide values are former and now already optimized future guide values, which are stored in the system.

In preferred embodiments, the conversion of the first data set comprises the step of deleting existing data and guide values; for example if a feedback of the second target group to these guide values are negative. They can preferably be provided with a lower loading and will therefore be labeled as possible solution for a problem, however not being an optimal solution or not being a solution suitable for a majority. In preferred embodiments, new guide values can be included if feedbacks of the second target group recommend such guide values or if there exist indications that such guide values may lead to a success when solving a problem. These processes are preferably fully automatic by using known and conventional statistical interpretation and evaluation methods.

A conversion of the second data set is preferably made in the same manner.

The system can therefore also be understood as a system for creating new guide values instead of a system for optimizing future guide values. The system is especially suitable for the above mentioned fields. However it can be used in other fields as well.

The system according to the invention for creating guide values comprises at least one first data set which comprises at least one first data group assigned to a first target group. The system furthermore comprises at least one second data set, which comprises at least one second data group assigned to a second target group. First data of the first target group are stored in the at least one first data group and second data of the second target group are stored in the at least one second data group. The system comprises a data processing unit for processing the first and second data and for output of the guide values to the second target group. According to the invention, the data processing unit is formed in order to receive new data generated on the basis of the output of the guide values to the second target group and on the basis of the use of these guide values in the second target group and in order to convert the first data set on the basis of these new data for the purpose of optimizing future guide values.

If the first target group is for example formed by mothers of infants, and the second by their infants, then for example discoveries and data of the pumping and giving of the pumped milk as well as health and development data of the infants may be entered into the data processing unit. These newly obtained data may be processed in the first data set; they are not simply just included. Rather, they lead to a conversion of the existing first data set. Various types of conversions will also be described below.

Particularly in the field of infant feeding with mother's milk and/or in the field of medical drainage, for example chest or wound drainage, the system according to the invention allows optimal advice and care of various target groups. In particular, it allows users of products or product systems to receive optimized instructions and product recommendations adapted individually to the requirements of the respective user. The system also makes it possible to adapt a device already in use optimally and individually to the requirements of the respective user. Since newly obtained data are entered back into the system and convert the first data set, the system is constantly improved. It is self-learning. This system can correct guide values which have been found to be suboptimal for particular situations, and an improved guide value can be given in the case of a closest similar case constellation.

The target groups preferably comprise human individuals or human types. The target groups may, however, also be device types, for example various types of breast pumps or medical drainage pumps. The first target group and the second target group may be different or identical. It is also possible for one of these two target groups to be a subset of the other of these two target groups. This means that a target group can be developed further and can further optimize its guide values by exchanging information and by processing the information within the system accordingly; this means by means of statistical and other assessment and evaluation of the entered and existing data.

When new data obtained from various target groups, in particular from initiators and receivers of guide values, are entered back into the system, an interactive system functioning in several or all directions is provided.

If a manufacturing company provides such a system to the users for their product range, individual users can benefit directly from experiences of other users. However, the system processes the empirical values or new data obtained, so that the user does not have to carry out their own qualitative evaluation, in contrast to the known experience sharing platforms.

If a manufacturing company provides this system to the users of its product range, then the user cannot only receive an individual recommendation of which product is optimal for him or her, but he or she can also receive individual recommendations for the use of this product. For example, taking into account her baby's status, a mother may communicate a particular breast pump and the parameters for operating the breast pump which are optimal for her as guide values. The parameters are, for example, reduced pressure to be selected and frequency of pumping, number and duration of pumping processes per day and addition of additives to the pumped mother's milk. Some or all of this information may for example also be entered directly into a programmable breast pump, as described for example in WO01/47577 in the name of the Applicant.

A further advantage is that the manufacturing company can optimize their quality assurance and their product development since they receive varied feedback.

Preferably, there are at least two first data groups and/or at least two second data groups, each data group being assigned to another target group. For example, mothers may be combined in subgroups as mothers with premature births, mothers with full-term births and mothers with induced births.

Preferably, there are at least two first data groups, the data processing unit being formed in order to convert one, several or all or a selectable number of the first data groups with the same new data. That is to say, discoveries from one target group may also influence the data set of another target group, so that the data set of this second target group can also be refined and improved.

In a preferred embodiment, the system is formed bidirectionally. To this end, the data processing unit is formed in order to output second guide values to the first target group, the data processing unit being formed in order to receive second new data generated on the basis of the output of the guide values to the first target group and on the basis of the use of these guide values in the first target group. The data processing unit is furthermore formed in order to convert the second data set on the basis of these second new data for the purpose of optimizing future second guide values. In this way, conversions and modifications in the data groups of the first target groups, for example the mothers, can be entered back into the data groups of the second target groups, for example the infants. This feedback, in particular also with different data groups of a data set, increases the learning effect of the system and therefore accelerates the optimization of the guide values.

Preferably, the system is formed in order to form further data groups for further target groups in accordance with new data and optionally in accordance with second new data. If the newly obtained data mean that subdivision of existing data groups or formation of an entirely new category of target groups is necessary, then depending on the embodiment the system will propose this automatically or automatically form this, or the system will prompt the formation of a new data group.

In a preferred embodiment, the conversion of the first and optionally of the second data set comprises at least one or more of the following actions: supplementing one or more data groups with further data, linking existing data with other existing data or further data, deleting existing data and/or existing links of data, creating a new data group, deleting an existing data group, creating a link between two data groups, deleting a link between two data groups, creating a new link with an existing guide value, deleting an existing link with an existing guide value, creating a new link with a guide value newly provided.

Preferably, the new data can be weighted in the conversion of the first data set, and optionally the second new data can be weighted during the conversion of the second data set. The weighting is carried out either automatically by the system, in accordance with previously entered values or by active input by a user of the system.

The guide values are preferably at least one or more of the following elements: treatment recommendations, material recommendations, product recommendations, dosing recommendations, control instructions for a device, regulating instructions for a device, a program for operating a device, application software (an app). Recommendations from the producer or the other mentioned guide values are given to the second target group. The feedbacks of this second target group are preferably automatically statistically analyzed and compared with the existing guide values. On this basis it is preferably decided in an automatic evaluation procedure, how a new or optimized guide value shall be. In the automatic evaluation procedure feedbacks, which occur several times in a similar form, are preferably more considered than feedbacks which are isolated and singular.

The system may be independent and, for example, available on the Internet and/or on known communication platforms such as Twitter or Facebook. As an alternative or in addition, however, it is preferably integrated in a device, and this device can be operated automatically in accordance with the system, in particular the guidelines received. For example, such a device is a breast pump for pumping human mother's milk or a drainage pump, for example for chest drainage, for wound drainage or for pumping bodily fluids out during operations, or for pumping out body fat.

If the system is not integrated in a device, it may preferably be put in communicating connection with such a device, the device being operatable automatically in accordance with the system. For example, by means of the system information can be stored on chip cards which can then be introduced into the device, for example the breast pump. Whole programs or individual control parameters may also be downloaded from the system into a control unit of the device, and stored therein. The transmission may be carried out in known ways, particularly via a cable connection or wirelessly.

The device is preferably, depending on the field of use of the system, a breast pump or another apparatus, which can be used in the field of use of the system.

If the system is integrated in a device, in a preferred embodiment it comprises the possibility of communicating with further devices and/or with sensors, or transmitting and/or receiving data to and from them.

In a preferred use of the invention, the system creates guide values in the field of infant feeding with human mother's milk, in particular by pumping mother's milk and bottle feeding of infants, the target groups being at least one or more of the following groups: breastfeeding mothers, non-breastfeeding mothers, mothers with naturally born babies, mothers with caesarean section, mothers with full-term births, mothers with induced births, mothers with premature births, mothers with single child birth, mothers with twins, mothers older than 40 years, mothers younger than 20 years, mothers between 20 and 40 years, fathers, family, premature births, normal births, infants with normal weight, overweight infants, underweight infants, infants with a specific deficiency, infants of a corresponding age, infants with special nutritional requirements.

The system may in particular in this case be part of a breast pump or it can be put in communicating connection with a breast pump, and/or it may create guide values for the operation of a breast pump.

The guide values preferably comprise at least one or more of the following elements: control data for a breast pump for pumping milk as painlessly as possible, control data for a breast pump for efficient pumping of mother's milk, control data for a breast pump for increasing the amount of milk, control data for a breast pump for reducing the amount of milk, recommendation of a breast pump type, recommendation of a nipple shield type, recommendation of times of day for pumping mother's milk, recommendation of a maximum duration of the pumping of mother's milk during a pumping session, recommendation of a teat type for a feeding bottle, recommendation for enrichment and/or for preparation of pumped mother's milk, recommendation for food supplement, time scheme for giving food to the infant.

As an alternative or in addition, the system creates guide values in the field of the drainage of bodily fluids, particularly chest drainage or wound drainage, the target groups being at least one or more of the following groups: patients, patients with specific deficiencies, patients of a specific age, patients with an illness having lasted for a defined time, patients with an illness in a particular body part, care personnel and surgeons, only care personnel, only surgeons.

The system may in this case be part of a drainage pump, or it may be possible to put it in communicating connection with a drainage pump, and/or it may create guide values for the operation of a drainage pump.

Other embodiments are specified in the dependent claims.

BRIEF DESCRIPTION OF THE DRAWINGS

Preferred embodiments of the invention will be described below with the aid of the appended drawing, which is used merely for explanation and is not to be interpreted restrictively. The single figure shows a schematic representation of the system according to the invention.

DESCRIPTION OF PREFERRED EMBODIMENTS

The single figure represents a greatly simplified representation of the system according to the invention. The system is shown as a rectangle with dashed lines.

The reference numeral 1 denotes a first data set, the reference numeral 2 denotes a second data set. There may also be further such data sets present.

Each data set 1, 2 comprises at least one, preferably two or more data groups 10, 20. Each data group is assigned to an external target group A, B.

The at least two data sets 1, 2 are connected to a data processing unit 3. In the data processing unit, guide values 30 are generated, or they are stored therein. The arrows 40, 50 respectively show a data transfer from the first and second data sets 1, 2 into the data processing unit 3. The arrows 60, 70 respectively show a first and a second guide value output to a first and second target group A, B, more precisely to an individual who fits into this target group. The arrows 61, 71 respectively show a first and a second transfer of new data which are returned from the target group A, B, more precisely from the corresponding individual, into the system, that is to say into the data processing unit 3. The arrows 41, 51 respectively show a first and a second conversion of the first and second data sets 1, 2 in accordance with the data processing unit 3 on the basis of the new data received.

Depending on the embodiment, the newly generated data may be read automatically into the data processing unit, for example by a sensor of a breast pump or drainage pump being used communicating a measurement value directly to the data processing unit, or by operating parameters of a drainage or breast pump being read directly into the system. Depending on the embodiment, the newly generated data may also be entered manually into the system, and thereby introduced into the data processing unit for further processing.

Some specific examples of use will be given below. The system according to the invention may consist of one, several or all of these examples in a single embodiment. The system may also comprise further examples, or consist entirely of other examples in the context of the invention described above.

EXAMPLE 1

The first data set comprises at least two first data groups, each first data group belonging to precisely one of the following target groups: mothers with full-term birth, mothers with premature birth. The data of the first data groups are: time until MER (from the first pumping movement to the milk flow); number of MER over a time profile; amount of milk per MER; vacuum strength in MER; duration of the individual MER. In this text, MER means milk ejection reflex.

The second data set comprises at least three second data groups, each second data group belonging to precisely one of the following target groups: underweight baby, baby with normal weight, overweight baby. The data of the first data groups are: milk consumption of the baby; age of the baby; weight of the baby; increase or decrease in weight since the last feed; data for the feeding method: via tube, via teat, via breast; drinking duration; ratio of amount of milk to drinking duration.

In a first data processing operation, the mothers in the two first data groups are assigned milk ejection reflex patterns (MER patterns). The babies are categorized in the second data groups. They are assigned a drinking bottle with a milk ejection reflex (MER) pattern as a function of their mothers. The guide values for the babies are therefore the MER drinking bottle types. The feedback to the system is experience gained when giving the milk with these selected drinking bottles.

EXAMPLE 2

The first data set comprises a first data group of a first target group: donors of mother's milk. The first data group comprises information about the composition of the milk and about the individual donors.

The second data set comprises a second data group of a second target group: babies with special nutritional requirements. The second data group contains information about these requirements and the necessary food compositions.

In a first data processing operation, the babies are categorized by assigning them a modified mother's milk which corresponds precisely to their requirements. The mothers use a breast pump whose operating parameter is adapted to the baby's requirements, so that mother's milk can be provided in a sufficient quantity with the required ingredients so as subsequently to synthesize the milk and enrich it with corresponding additives. The guide values are therefore the operating parameters for the breast pump and the information about the required composition of the milk. The feedback to the system is information about the amount of milk and milk composition actually obtained during the pumping.

In a second or alternative data processing operation, the milk mixture which is optimal for a specific baby is determined from the pool of donor milk. These indications are output as guide values so that his food can also actually be mixed and administered to him. Information about the development of the baby, or about any complications such as stomach cramps or rashes, is reported back to the system as new data.

EXAMPLE 3

The first data set comprises two first data groups, each being assigned to a first target group: mothers with premature births, the premature births having required intensive care; donors of mother's milk. The first data group comprises information about the composition of the milk of the mothers with premature births and the donors.

The second data set comprises a second data group of a second target group: premature births with special nutritional requirements. The second data group contains information about these requirements and the necessary food compositions.

In the data processing operation, an evaluation is made as to the enrichment which the milk of a specific real mother requires, and the information about how to carry out this enrichment and with which donor milk the desired result is achieved is delivered as guidelines.

Information about the development of the baby, or about any complications such as stomach cramps or rashes, is reported back to the system as new data.

EXAMPLE 4

The first data set comprises two first data groups, each being assigned to a first target group: mothers with low milk production; mothers who used to have low milk production but have overcome this. The first data group comprises information about the amount of milk which is produced over 24 hours in the mother's body, and information about the time profile of obtaining the milk and the amount of milk.

The second data set comprises a second data group of a second target group: mothers with low milk production. The second data group contains similar information.

In the data processing operation, an evaluation is made as to which factors could raise the milk production and these are output as guide values. The guide values may therefore comprise: parameters for operation of the milk pump, optimal type of milk pump, optimal nipple shield, pumping scheme with durations and intervals between the individual pumping processes, positioning of the mother during the pumping, environmental setting.

Information about parameters and parameter groups which have led to an increase in milk production, or which did not or produced a negative effect, is reported back to the system as new data.

EXAMPLE 5

The first data set comprises two first data groups, each being assigned to a first target group: care personnel of chest patients, surgeons of chest patients. The first data group comprises information about the data set of previous patients and about their healing profile over a period of time, particularly over a prolonged time.

The second data set comprises a second data group of a second target group: chest patients. The second data group contains information about secretion drainage/secretion reduction over a period of time considered, for example over 24 hours.

In the data processing operation, with the aid of known profiles of other cases, an evaluation is made as to how the specific healing process might develop. On the basis thereof, the optimal form of therapy for the specific patient is established. As possible guide values, the system therefore indicates medicament data and dosages, parameters for operation of the chest drainage pump.

Information about the healing outcome or problems during the healing of the specific patient is reported back to the system as new data.

The system according to the invention allows simply usable and individually optimized instruction for individuals and users, which is based on the experience of many people before.

What is claimed is:

1. A system for optimizing future guide values, comprising:
    at least one first data set which comprises at least one first data group assigned to a first target group,
    at least one second data set, which comprises at least one second data group assigned to a second target group,
    wherein first data of the first target group are stored in the at least one first data group and second data of the second target group are stored in the at least one second data group, and a data processing unit for processing the first and second data and for output of existing guide values to the second target group,
    wherein the data processing unit is formed in order to receive new data generated on the basis of the output of the guide values to the second target group and on the basis of the use of these guide values in the second target group and in order to convert the first data set on the basis of these new data for the purpose of optimizing future guide values, wherein the system creates guide values in the field of infant feeding with human mother's milk, the target groups being at least one of the following groups: breastfeeding mothers, non-breastfeeding mothers, mothers with naturally born babies, mothers with Caesarean section, mothers with full-term births, mothers with induced births, mothers with premature births, mothers with single child birth, mothers with twins, mothers older than 40 years, mothers younger than 20 years, mothers between 20 and 40 years, fathers, family, premature births, normal births, infants with normal weight, overweight infants, underweight infants, infants with a specific deficiency, infants of a corresponding age, infants with special nutritional requirements.

2. The system according to claim 1, wherein there are at least two first data groups and/or at least two second data groups, each data group being assigned to another target group.

3. The system according to claim 1, wherein there are at least two first data groups, and wherein the data processing unit is formed in order to convert one, several or all or a selectable number of the first data groups with the same new data.

4. The system according to claim 1, wherein the data processing unit is formed in order to output second guide values to the first target group, and wherein the data processing unit is formed in order to receive second new data generated on the basis of the output of the guide values to the first target group and on the basis of the use of these guide values in the first target group, the data processing unit furthermore being formed in order to convert the second data set on the basis of these second new data for the purpose of optimizing future second guide values.

5. The system according to claim 4, wherein the system is formed in order to form further data groups for further target groups in accordance with the new data and in accordance with the second new data.

6. The system according to claim 1, wherein the system is formed in order to form further data groups for further target groups in accordance with the new data.

7. The system according to claim 1, wherein the new data is weighted in the conversion of the first data set.

8. The system according to claim 7, wherein the second new data is weighted during the conversion of the second data set.

9. The system according to claim 1, wherein the first target group and the second target group are identical, or wherein one of these two target groups is a subset of the other of these two target groups.

10. The system according to claim 1, wherein the guide values are at least one of the following: treatment recommendations, material recommendations, product recommendations, dosing recommendations, control instructions for a device, regulating instructions for a device, a program for operating a device, application software.

11. The system according to claim 1, wherein the system is integrated in a device, and this device is operated automatically in accordance with the system.

12. The system according to claim 1, wherein the system is in selective communicating connection with a device, the device being operatable automatically in accordance with the system.

13. The system according to claim 1, wherein the system is part of a breast pump, is in selective communicating connection with a breast pump, and/or creates guide values for the operation of a breast pump.

14. The system according to claim 1, wherein the guide values comprise at least one of the following elements: control data for a breast pump for pumping milk as painlessly as possible, control data for a breast pump for efficient pumping of mother's milk, control data for a breast pump for increasing the amount of milk, control data for a breast pump for reducing the amount of milk, recommendation of a breast pump type, recommendation of a nipple shield type, recommendation of times of day for pumping mother's milk, recommendation of a maximum duration of the pumping of mother's milk during a pumping session, recommendation of a teat type for a feeding bottle, recommendation for enrichment and/or for preparation of pumped mother's milk, recommendation for food supplement, time scheme for giving food to the infant.

15. The system according to claim 1, wherein the at least one first data set, the at least one second data set and the first target group and the second target group are of the field of infant feeding with mother's milk.

16. A system for optimizing future guide values, comprising:

at least one first data set which comprises at least one first data group assigned to a first target group, at least one second data set, which comprises at least one second data group assigned to a second target group, wherein first data of the first target group are stored in the at least one first data group and second data of the second target group are stored in the at least one second data group, and a data processing unit for processing the first and second data and for output of existing guide values to the second target group, wherein the data processing unit is formed in order to receive new data generated on the basis of the output of the guide values to the second target group and on the basis of the use of these guide values in the second target group and in order to convert the first data set on the basis of these new data for the purpose of optimizing future guide values, wherein the guide values comprise at least one of the following elements: control data for a breast pump for pumping milk as painlessly as possible, control data for a breast pump for efficient pumping of mother's milk, control data for a breast pump for increasing the amount of milk, control data for a breast pump for reducing the amount of milk, recommendation of a breast pump type, recommendation of a nipple shield type, recommendation of times of day for pumping mother's milk, recommendation of a maximum duration of the pumping of mother's milk during a pumping session, recommendation of a teat type for a feeding bottle, recommendation for enrichment and/or for preparation of pumped mother's milk, recommendation for food supplement, time scheme for giving food to the infant.

17. The system according to claim 16, wherein there are at least two first data groups and/or at least two second data groups, each data group being assigned to another target group.

18. The system according claim 16, wherein there are at least two first data groups, and wherein the data processing unit is formed in order to convert one, several or all or a selectable number of the first data groups with the same new data.

19. The system according to claim 16, wherein the data processing unit is formed in order to output second guide values to the first target group, and wherein the data processing unit is formed in order to receive second new data generated on the basis of the output of the guide values to the first target group and on the basis of the use of these guide values in the first target group, the data processing unit furthermore being formed in order to convert the second data set on the basis of these second new data for the purpose of optimizing future second guide values.

20. The system according to claim 19, wherein the system is formed in order to form further data groups for further target groups in accordance with the new data and in accordance with the second new data.

21. The system according to claim 16, wherein the system is formed in order to form further data groups for further target groups in accordance with the new data.

22. The system according to claim 16, wherein the new data is weighted in the conversion of the first data set.

23. The system according to claim 22, wherein the second new data is weighted during the conversion of the second data set.

24. The system according to claim 16, wherein the first target group and the second target group are identical, or wherein one of these two target groups is a subset of the other of these two target groups.

25. The system according to claim 16, wherein the guide values are at least one of the following: treatment recommendations, material recommendations, product recommendations, dosing recommendations, control instructions for a device, regulating instructions for a device, a program for operating a device, application software.

26. The system according to claim 16, wherein the system is integrated in a device, and this device can be is operated automatically in accordance with the system.

27. The system according to claim 16, wherein the system is in selective communicating connection with a device, the device being operatable automatically in accordance with the system.

28. The system according to claim 16, wherein the system is part of a breast pump, is in selective communicating connection with a breast pump, and/or creates guide values for the operation of a breast pump.

29. The system according to claim 16, wherein the at least one first data set, the at least one second data set and the first target group and the second target group are of the field of infant feeding with mother's milk.

* * * * *

UNITED STATES PATENT AND TRADEMARK OFFICE
CERTIFICATE OF CORRECTION

PATENT NO. : 10,037,354 B2
APPLICATION NO. : 15/025439
DATED : July 31, 2018
INVENTOR(S) : Erich Pfenniger et al.

Page 1 of 1

It is certified that error appears in the above-identified patent and that said Letters Patent is hereby corrected as shown below:

In the Claims

At Column 11, Line 1, "according claim" should be -- according to claim --.

At Column 12, Line 13, "be is operated" should be -- be operated --.

Signed and Sealed this
Eighth Day of January, 2019

Andrei Iancu
*Director of the United States Patent and Trademark Office*